(12) United States Patent
Merkle et al.

(10) Patent No.: US 6,538,135 B1
(45) Date of Patent: Mar. 25, 2003

(54) METHOD FOR PRODUCING 4-AMINO-5-CHLORO-1-PHENYL PYRIDAZINONE-(6)

(75) Inventors: Hans Rupert Merkle, Ludwigshafen (DE); Klaus Herbig, Schifferstadt (DE); Erich Fretschner, Neckarsteinach (DE); Helmut Fröhlich, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/937,812

(22) PCT Filed: Mar. 30, 2000

(86) PCT No.: PCT/EP00/02827

§ 371 (c)(1),
(2), (4) Date: Sep. 28, 2001

(87) PCT Pub. No.: WO00/59891

PCT Pub. Date: Oct. 12, 2000

(30) Foreign Application Priority Data

Mar. 31, 1999 (DE) .......................................... 199 14 722

(51) Int. Cl.⁷ ............................................. C07D 237/14
(52) U.S. Cl. ....................................................... 544/241
(58) Field of Search ......................................... 544/241

(56) References Cited

U.S. PATENT DOCUMENTS

| 4,297,493 A | 10/1981 | Richarz et al. ............. 544/241 |
| 4,454,318 A | 6/1984 | Clauson-Kaas et al. ..... 544/241 |

FOREIGN PATENT DOCUMENTS

| GB | 871674 | 6/1961 |
| GB | 1124398 | 8/1968 |

OTHER PUBLICATIONS

Abstract for DL 131 172 (Jun. 1978).

*Primary Examiner*—Emily Bernhardt
(74) *Attorney, Agent, or Firm*—Keil & Weinkauf

(57) ABSTRACT

In a process for preparing 4-amino-5-chloro-1-phenylpyridazin-6-one by reacting 4,5-dichloro-1-phenylpyridazin-6-one with aqueous ammonia in the presence of a catalyst, the catalyst used is soluble in the aqueous alkaline reaction medium but is essentially insoluble in the reaction medium which has been acidified after removal of the 4-amino-5-chloro-1-phenylpyridazin-6-one.

The process of the present invention makes it possible for the catalyst to be recovered and reused in a simple manner.

5 Claims, No Drawings

METHOD FOR PRODUCING 4-AMINO-5-CHLORO-1-PHENYL PYRIDAZINONE-(6)

The present invention relates to a process for preparing 4-amino-5-chloro-1-phenylpyridazin-6-one by reacting 4,5-dichloro-1-phenylpyridazin-6-one with aqueous ammonia in the presence of a catalyst.

4-Amino-5-chloro-1-phenylpyridazin-6-one (chloridazon) is used as a herbicide for selective control of weeds in sugar beet. This compound is prepared as described in GB 871674 by reacting 4,5-dichloro-1-phenylpyridazin-6-one with aqueous ammonia under pressure and at elevated temperature. This gives an isomer mixture of about 80% by weight of 4-amino-5-chloro-1-phenylpyridazin-6-one and about 20% by weight of 5-amino-4-chloro-1-phenylpyridazin-6-one. The isolation of the chloridazon from this isomer mixture by extraction of the undesired isomer with nonpolymer solvents is described, for example, in DE 16 20 186.

Furthermore, attempts have been made to carry out the reaction in such a way that a purer product is obtained. Thus, DD 131172 describes the above reaction in organic solvents, which gives a purer product. However, the use of organic solvents in place of water is a drawback. EP 26 847 A and EP 28 359 A describe the reaction of 4,5-dichloro-1-phenylpyridazin-6-one with aqueous ammonia under pressure in the presence of phenolic compounds having substituents which make these compounds soluble in the aqueous reaction medium. Examples of such compounds are 4-phenolsulfonic acid, 3-hydroxypyridone and 3-hydroxypyridine. very good yields of chloridazon of high purity are obtained in this way. The catalysts used cannot be reused in the form of the solution in the reaction medium because this would involve recirculation of the ammonium chloride formed in the reaction. On the other hand, recovery of the catalysts from the aqueous reaction medium is possible to only a very limited extent, even by extraction with organic solvents, because of their high solubility in water.

It is an object of the present invention to provide a process for preparing chloridazon in which the chloridazon is obtained in high yield and high purity and the catalyst employed can be reused in a simple manner.

We have found that this object is achieved by a process in which 4,5-dichloro-1-phenylpyridazin-6-one is reacted with aqueous ammonia in the presence of a catalyst which is soluble in the reaction medium used but is essentially insoluble in the reaction medium at an acid pH.

The present invention accordingly provides a process for preparing 4-amino-5-chloro-1-phenylpyridazin-6-one by reacting 4,5-dichloro-1-phenylpyridazin-6-one with aqueous ammonia in the presence of a catalyst which is soluble in the aqueous reaction medium used (i.e. at an alkaline pH) but is essentially insoluble in the reaction medium which has been acidified after removal of the precipitated 4-amino-5-chloro-1-phenylpyridazin-6-one.

The ammonia is used in a large excess for the reaction. The pH of the aqueous reaction medium is thus in the alkaline range. The catalysts used here are soluble in this reaction medium.

If desired, the excess ammonia is removed after the reaction, e.g. by stripping before or during cooling of the reaction mixture.

The chloridazon obtained precipitates as a solid after the reaction, particularly on cooling the reaction mixture. It is isolated from the reaction medium in a customary manner, for example by filtration. The reaction medium remaining after isolation of the chloridazon (mother liquor) has an alkaline pH. Setting of an acid pH, for example pH<6, in particular <4 and particularly preferably <2, by means of an inorganic acid such as hydrochloric acid, sulfuric acid or phosphoric acid or an organic acid such as formic acid or acetic acid makes the catalyst insoluble in the reaction medium. In general, it precipitates as an amorphous or crystalline solid and can thus be isolated in a simple manner, for example by filtration. For the purposes of the present invention, "insoluble in the reaction medium" means that the catalyst has a solubility in the reaction medium of not more than 5 g/l, in particular not more than 2 g/l.

Suitable catalysts are, in particular, phenolic compounds whose aromatic ring system is substituted not only by the phenolic hydroxy group but also by at least one further electron-withdrawing substituent without acidic hydrogen atoms. For the purposes of the present invention, phenolic compounds are compounds having an aromatic carbocyclic or heterocyclic ring system (in particular phenyl, naphthyl, pyridyl, pyrimidyl, etc.) which bears at least one hydroxy group.

The aromatic ring system generally bears one or two electron-withdrawing substituents. These are, in particular, $SO_2R^1$, $NO_2$, $COR^1$, $CF_3$, $CN$ and $OR^1$, where $R^1$ is $C_1$–$C_6$-alkyl or phenyl which may be substituted by 1 or 2 hydroxy groups.

Phenolic compounds which can be used are, for example, 2-, 3- or 4-nitrophenol, 2,4-dinitrophenol, 4-benzoylphenol, 4,4'-dihydroxybenzophenone and, in particular, bis(hydroxyphenyl)sulfones such as bis(4-hydroxyphenyl) sulfone.

The salts of the phenolic compounds, e.g. the alkali metal or alkaline earth metal salts and the ammonium salts, are also suitable.

The phenolic compounds are water-soluble in the phenoxide form but are essentially water-insoluble in the form of the free phenols. They can therefore be recovered essentially quantitatively, but at least to an extent of 80%, in particular at least 90%, and be used for further reactions. In this way, they are also separated from the ammonium chloride formed in the reaction. Addition of bases such as aqueous sodium hydroxide to the reaction medium obtained after recovery of the catalyst enables the ammonia bound in the form of ammonium chloride to be liberated again and recovered.

The reaction of 4,5-dichloro-1-phenylpyridazin-6-one with ammonia can be carried out in one or two stages. In the single-stage variant, the reactants and the catalyst are introduced simultaneously. In the two-stage variant, a solution of the catalyst, for example a solution of a sodium or ammonium salt of the catalyst, is first reacted with 4,5-dichloro-1-phenylpyridazin-6-one so as to replace the chlorine atom in the 4 position by the corresponding phenoxide to give the corresponding intermediate. For example, when bis(4-hydroxyphenyl)sulfone is used as catalyst, 4-(4-hydroxyphenylsulfonyl)phenyloxy-5-chloro-1-phenylpyridazin-6-one is obtained as intermediate. The respective intermediate is subsequently reacted with aqueous ammonia under pressure to convert it into the desired chloridazon product.

The process of the present invention is generally carried out in the temperature range from 80 to 200° C., in particular from 100 to 150° C. and preferably from 100 to 140° C.

The amount of catalyst employed can be varied within a wide range. The reaction is advantageously carried out in the presence of from 1 to 200 mol %, in particular from 20 to 150 mol %, of catalyst, based on 4,5-dichloro-1-phenylpyridazin-6-one.

The process is carried out at a pressure which is generally in the range from 1 to 50 bar, preferably from 3 to 20 bar. The process is particularly preferably carried out at the pressure established in the closed reaction vessel at the reaction temperature selected. However, it is also possible to increase the pressure in the closed vessel during the reaction by injection of ammonia. In this case, part of the injected ammonia dissolves in the aqueous reaction medium.

The following examples illustrate the invention without limiting it in any way.

EXAMPLE 1

Preparation of 4-amino-5-chloro-1-phenylpyridazin-6-one (chloridazon) using bis(4-hydroxyphenyl)sulfone In a 250 ml stirring autoclave, 100 parts of water, 70 parts (1.03 mol) of 25% strength ammonia, 12 parts (0.05 mol) of 4,5-dichloro-1-phenylpyridazin-6-one (purity: 99.7%) and 12.5 parts (0.05 mol) of bis(4-hydroxyphenyl)sulfone were stirred at 130° C. for 8 hours. The pressure rose steadily to about 5 bar. After stirring overnight, the autoclave was depressurized to atmospheric pressure, with the excess ammonia being stripped off. After cooling to room temperature, the precipitated solid was filtered off, washed with water and dried at 50° C. in a vacuum drying oven.

This gave 10.1 parts of 4-amino-5-chloro-1-phenylpyridazin-6-one having a purity of 98.8%; this corresponds to a yield of 90% of theory. The pH of the filtrate was adjusted to 1.5 using 60% strength sulfuric acid and the precipitated bis(4-hydroxyphenyl)sulfone was filtered off, washed with water and dried. This gave 12.6 parts of bis(4-hydroxyphenyl)sulfone having a purity of 99.2%; this corresponds to 100% of the amount of catalyst used.

EXAMPLE 2

Preparation of 4-amino-5-chloro-1-phenylpyridazin-6-one (chloridazon) using bis(4-hydroxyphenyl)sulfone as catalyst In a 1 l stirring autoclave, 300 parts of water, 210 parts (3.09 mol) of 25% strength ammonia, 36 parts (0.15 mol) of 4,5-dichloro-1-phenylpyridazin-6-one (purity: 99.7%) and 37.5 parts (0.15 mol) of bis(4-hydroxyphenyl)sulfone were stirred at 130° C. for 8 hours. The pressure rose steadily to about 5 bar. After stirring overnight, the autoclave was depressurized to atmospheric pressure, with the excess ammonia being stripped off. After cooling to room temperature, the precipitated solid was filtered off, washed with water and dried at 50° C. in a vacuum drying oven.

This gave 30.7 parts of 4-amino-5-chloro-1-phenylpyridazin-6-one having a purity of 99.9%; this corresponds to a yield of 92.3% of theory. The pH of the filtrate was adjusted to 1.4 using 60% strength sulfuric acid and the precipitated bis(4-hydroxyphenyl)sulfone was filtered off and washed with water. This gave 53.5 parts of bis(4-hydroxyphenyl)sulfone having a water content of 30%. This corresponds to 99.8% of the amount of catalyst used.

EXAMPLE 3

Preparation of 4-amino-5-chloro-1-phenylpyridazin-6-one using recycled bis(4-hydroxyphenyl)sulfone The moist catalyst from Example 2 was stirred at 130° C. with 300 parts of water, 210 parts (3.09 mol) of 25% strength ammonia and 36 parts (0.15 mol) of 4,5-dichloro-1-phenylpyridazin-6-one (purity: 99.7%) for 8 hours in the 1 l stirring autoclave. A pressure of 6 bar was established. After stirring overnight, the autoclave was depressurized to atmospheric pressure, with the excess ammonia being stripped off. After cooling to room temperature, the precipitated solid was filtered off, washed with water and dried at 50° C. in a vacuum drying oven.

This gave 30.5 parts of 4-amino-5-chloro-1-phenylpyridazin-6-one having a purity of 99.5%; this corresponds to a yield of 91.3% of theory. The pH of the filtrate was adjusted to 1.4 using 60% strength sulfuric acid and the precipitated bis(4-hydroxyphenyl)sulfone was filtered off, washed with water and dried. This gave 37.1 parts of bis(4-hydroxyphenyl)sulfone having a purity of 99.5%; this corresponds to 98.4% of the amount of catalyst used.

EXAMPLE 4

Preparation of 4-amino-5-chloro-1-phenylpyridazin-6-one (chloridazon) using 4-nitrophenol as catalyst In a 250 ml stirring autoclave, 100 parts of water, 70 parts (1.03 mol) of 25% strength ammonia, 12 parts (0.05 mol) of 4,5-dichloro-1-phenylpyridazin-6-one (purity: 99.7%) and 14.2 parts (0.1 mol) of 98%-pure 4-nitrophenol were stirred at 130° C. for 8 hours. The pressure rose to about 4 bar. After stirring overnight, the autoclave was depressurized to atmospheric pressure, with the excess ammonia being stripped off. After cooling to room temperature, the precipitated solid was filtered off, washed with water and dried at 50° C. in a vacuum drying oven.

This gave 10.3 parts of 4-amino-5-chloro-1-phenylpyridazin-6-one having a purity of 99.1%; this corresponds to a yield of 92.2% of theory. The pH of the filtrate was adjusted to 1.0 using 60% strength sulfuric acid and the precipitated 4-nitrophenol was filtered off, washed with water and dried. This gave 14 parts of 4-nitrophenol having a purity of 98.1%; this corresponds to 98.8% of the amount of catalyst used.

EXAMPLE 5

Preparation of 4-amino-5-chloro-1-phenylpyridazin-6-one (chloridazon) using 4,4'-dihydroxybenzophenone as catalyst In a 250 ml stirring autoclave, 100 parts of water, 70 parts (1.03 mol) of 25% strength ammonia, 12 parts (0.05 mol) of 4,5-dichloro-1-phenylpyridazin-6-one (purity: 99.7%) and 10.7 parts (0.05 mol) of 4,4'-dihydroxybenzophenone were stirred at 130° C. for 8 hours. The pressure rose steadily to about 4.5 bar. After stirring overnight, the autoclave was depressurized to atmospheric pressure, with the excess ammonia being stripped off. After cooling to room temperature, the precipitated solid was filtered off, washed with water and dried at 50° C. in a vacuum drying oven.

This gave 10.2 parts of 4-amino-5-chloro-1-phenylpyridazin-6-one having a purity of 98.9%; this corresponds to a yield of 91.1% of theory. The pH of the filtrate was adjusted to 1.5 using 60% strength sulfuric acid and the precipitated 4,4'-dihydroxybenzophenone was filtered off, washed with water and dried. This gave 10.9 parts of 4,4'-dihydroxybenzophenone having a purity of 98.3%; this corresponds to 100% of the amount of catalyst used.

EXAMPLE 6

Preparation of 4-amino-5-chloro-1-phenylpyridazin-6-one (chloridazon) using recycled 4,4'-dihydroxybenzophenone as catalyst The catalyst from Example 5 was stirred at 130° C. with 100 parts of water, 70 parts (1.03 mol) of 25% strength ammonia and 12 parts (0.05 mol) of 4,5-dichloro-1-phenylpyridazin-6-one (purity: 99.7%) for 8 hours in a 250 ml stirring autoclave. A pressure of 4.3 bar was established. After stirring overnight, the autoclave was depressurized to atmospheric pressure, with the excess ammonia being stripped off. After cooling to room temperature, the precipitated solid was filtered off, washed with water and dried at 50° C. in a vacuum drying oven.

This gave 10 parts of 4-amino-5-chloro-1-phenylpyridazin-6-one having a purity of 99.1%; this corresponds to a yield of 89.5% of theory. The pH of the filtrate was adjusted to 1.5 using 60% strength sulfuric acid and the precipitated 4,4'-dihydroxybenzophenone was filtered off, washed with water and dried. This gave 10.7 parts of 4,4'-dihydroxybenzophenone having a purity of 99.2%; this corresponds to 99.2% of the amount of catalyst used.

We claim:

1. A process for preparing 4-amino-5-chloro-1-phenylpyridazin-6-one comprising
   a) reacting 4,5-dichloro-1-phenylpyridazin-6-one with aqueous ammonia in the presence of a catalyst which is soluble in the aqueous alkaline reaction medium but becomes essentially insoluble in the reaction medium when this is being acidified,
   b) removing the precipitated 4-amino-5-chloro-1-phenylpyridazin-6-one,
   c) acidifying the reaction medium, and
   d) isolating the precipitated catalyst,
   wherein the catalyst used is a carbocyclic phenolic compound or a salt thereof, whose aromatic ring system is substituted not only by the phenolic hydroxy group or groups but also by at least one further electron-withdrawing substituent without acidic hydrogen atoms, selected from $SO_2R^1$, $NO_2$, $COR^1$, $CF_3$ or $CN$, where $R^1$ is $C_1$–$C_6$-alkyl or phenyl which may be substituted by 1 or 2 hydroxy groups.

2. A process as claimed in claim 1, wherein the catalyst used is bis(4-hydroxyphenyl)sulfone, 2-, 3- or 4-nitrophenol or 2,4-dinitrophenol.

3. A process as claimed in claim 1, wherein the catalyst is used in an amount of from 1 to 200 mol %, based on 4,5-dichloro-1-phenylpyridazin-6-one.

4. A process as claimed in claim 1, wherein the reaction is carried out at a temperature in the range from 80 to 200° C.

5. A process as claimed in claim 1, wherein the reaction is carried out at a pressure in the range from 1 to 50 bar.

* * * * *